US010783637B2

(12) United States Patent
Li

(10) Patent No.: US 10,783,637 B2
(45) Date of Patent: Sep. 22, 2020

(54) LEARNING DATA GENERATION SUPPORT APPARATUS, LEARNING DATA GENERATION SUPPORT METHOD, AND LEARNING DATA GENERATION SUPPORT PROGRAM

(71) Applicant: FUJIFILM Corporation, Tokyo (JP)

(72) Inventor: Yuanzhong Li, Tokyo (JP)

(73) Assignee: FUJIFILM Corporation, Minato-Ku, Tokyo (JP)

(*) Notice: Subject to any disclaimer, the term of this patent is extended or adjusted under 35 U.S.C. 154(b) by 115 days.

(21) Appl. No.: 15/987,423

(22) Filed: May 23, 2018

(65) Prior Publication Data
US 2018/0365834 A1 Dec. 20, 2018

(30) Foreign Application Priority Data

Jun. 20, 2017 (JP) ................. 2017-120497

(51) Int. Cl.
*G06T 7/00* (2017.01)
*G06K 9/66* (2006.01)
(Continued)

(52) U.S. Cl.
CPC ............. *G06T 7/0016* (2013.01); *G06K 9/66* (2013.01); *G06N 3/08* (2013.01); *G06N 20/00* (2019.01); *G16H 30/20* (2018.01); *G16H 30/40* (2018.01); *G16H 50/20* (2018.01); *G06F 40/20* (2020.01); *G06K 9/6201* (2013.01);
(Continued)

(58) Field of Classification Search
CPC .... G06K 2209/05; G06K 9/6201; G06K 9/66; G06T 7/0016
See application file for complete search history.

(56) References Cited

U.S. PATENT DOCUMENTS 8,423,571 B2    4/2013   Moriya
8,705,820 B2    4/2014   Moriya
(Continued)

FOREIGN PATENT DOCUMENTS

JP    2009-082441 A    4/2009
JP    2009-086750 A    4/2009
(Continued)

OTHER PUBLICATIONS

Communication dated Jan. 7, 2020, from the Japanese Patent Office in application No. 2017-120497.

*Primary Examiner* — John J Lee
(74) *Attorney, Agent, or Firm* — Sughrue Mion, PLLC

(57) ABSTRACT

Extraction means analyzes a character string of an interpretation report to extract lesion portion information recorded in the interpretation report and a first lesion feature recorded in the interpretation report, and analysis means performs an image analysis process corresponding to the lesion portion information with respect to the image data corresponding to the interpretation report to acquire a second lesion feature based on a result of the image analysis process. Determination means determines whether the first lesion feature matches the second lesion feature, and registration means registers the image data corresponding to the interpretation report as learning correct answer data in a case where it is determined that the first lesion feature matches the second lesion feature.

10 Claims, 4 Drawing Sheets

(51) Int. Cl.
  *G06N 20/00* (2019.01)
  *G06N 3/08* (2006.01)
  *G16H 50/20* (2018.01)
  *G16H 30/40* (2018.01)
  *G16H 30/20* (2018.01)
  *G06K 9/62* (2006.01)
  *G06N 3/04* (2006.01)
  *G06F 40/20* (2020.01)

(52) U.S. Cl.
  CPC ....... *G06K 2209/05* (2013.01); *G06N 3/0454* (2013.01); *G06T 2207/20081* (2013.01); *G06T 2207/30096* (2013.01)

(56) References Cited

U.S. PATENT DOCUMENTS

| | | | |
|---|---|---|---|
| 8,837,794 B2 | 9/2014 | Nakamura | |
| 10,158,505 B2 * | 12/2018 | Sin | G05B 19/054 |
| 2010/0256459 A1 * | 10/2010 | Miyasa | G06F 19/321 |
| | | | 600/300 |
| 2010/0256991 A1 | 10/2010 | Ishikawa et al. | |

FOREIGN PATENT DOCUMENTS

| | | |
|---|---|---|
| JP | 2011-062283 A | 3/2011 |
| JP | 2011-092682 A | 5/2011 |
| JP | 2011-092684 A | 5/2011 |
| JP | 2013-149256 A | 8/2013 |
| JP | 2015-191561 A | 11/2015 |

\* cited by examiner

LEARNING DATA GENERATION SUPPORT APPARATUS, LEARNING DATA GENERATION SUPPORT METHOD, AND LEARNING DATA GENERATION SUPPORT PROGRAM

CROSS-REFERENCE TO RELATED APPLICATION

This application claims priority from Japanese Patent Application No. 2017-120497, filed on Jun. 20, 2017, the disclosure of which is incorporated by reference herein in its entirety.

BACKGROUND

Field of the Invention

The present invention relates to a learning data generation support apparatus, a learning data generation support method, and a learning data generation support program that perform support for generating learning data through machine learning.

Related Art

In the related art, machine learning has been used for learning features of data to perform recognition or classification of images or the like. In recent years, various learning methods have been developed, and as a processing capability of a computer has been enhanced, a processing time has been reduced. Furthermore, a system has been able to perform deep learning for learning features of image data or the like at a deeper level. By performing the deep learning, it is possible to recognize features of images or the like with extremely high accuracy, and thus, it is expected that discrimination performance is enhanced. A large amount of various data is necessary for the deep learning, and data for discrimination of a large number of images is acquired through the Internet or the like.

On the other hand, in accordance with the spread of a medical information system, for the purpose of cooperation of disease diagnosis and sharing of medical information in districts, realization of a wide range electronic medical record in which data exchange is possible between medical organizations has been performed. As an elemental technology of a wide range electronic medical record system, there is a medical image management system (PACS: picture archiving and communication system) provided in each medical organization. The PACS performs storage, browsing, and management of image data received from an imaging apparatus (modality) such as a computed radiography (CR) apparatus, a computed tomography (CT) apparatus, and a magnetic resonance imaging (MRI) apparatus. Further, by managing image data using the DICOM (digital imaging and communication in medicine) standard, it is possible to unitarily manage various kinds of image data.

Further, in the medical image management system, an interpretation report obtained by interpretation of images captured by various modalities from a radiologist is stored in association with image data thereof. An interpretation result recorded in the interpretation report is important for diagnosis, and thus, it is desirable that an accurate interpretation result is recorded. In order to reduce omission of interpretation or to lighten a burden on a doctor, a system that discriminates the type of a lesion detected by performing image processing with respect to image data and supports creation of a report by providing the discrimination result has been proposed. Alternatively, a system that detects a difference between analysis result information extracted from interpretation report information that is an interpretation result obtained from a doctor and diagnosis support information has been proposed (For example, JP2013-149256A and JP2009-082441A).

In the medical field, similarly, it is desirable to recognize features of images or the like with high accuracy using deep learning or the like. For the deep learning, learning based on a large amount of high-quality data is essential, as necessary. In the medical field, it may be considered that data necessary for learning is buried in a large amount of data stored in a medical image management system, and thus, a method for acquiring data to be used in deep learning from image data stored in a medical information system has been reviewed. However, it is not rational to manually discriminate correct answer data from the large amount of data. On the other hand, there are many cases where correct information is recorded in an interpretation report obtained by a skilled radiologist, and thus, it is possible to obtain a correct result in consideration of previous interpretation reports.

SUMMARY

In order to solve the above-described problems, an object of the invention is to provide a learning data generation support apparatus, a learning data generation support method, and a learning data generation support program for providing a large amount of various image data necessary for deep learning in a medical field.

According to an aspect of the invention, there is provided a learning data generation support apparatus comprising: storage means for storing a plurality of pieces of image data and an interpretation report with respect to each of the plurality of pieces of image data; extraction means for analyzing a character string of the interpretation report to extract lesion portion information recorded in the interpretation report and a first lesion feature recorded in the interpretation report; analysis means for performing an image analysis process corresponding to the lesion portion information with respect to the image data corresponding to the interpretation report to acquire a second lesion feature based on a result of the image analysis process; determination means for determining whether the first lesion feature matches the second lesion feature; and registration means for registering the image data corresponding to the interpretation report as learning correct answer data in a case where it is determined that the first lesion feature matches the second lesion feature.

According to another aspect of the invention, there is provided a learning data generation support method using a learning data generation support apparatus including storage means for storing a plurality of pieces of image data and an interpretation report with respect to each of the plurality of pieces of image data, extraction means, analysis means, determination means, and registration means, the method comprising: an extraction step of analyzing a character string of the interpretation report to extract lesion portion information recorded in the interpretation report and a first lesion feature recorded in the interpretation report, using the extraction means; an analysis step of performing an image analysis process corresponding to the lesion portion information with respect to the image data corresponding to the interpretation report to acquire a second lesion feature based on a result of the image analysis process, using the analysis means; a determination step of determining whether or not the first lesion feature matches the second lesion feature, using the determination means; and a registration step of registering the image data corresponding to the interpretation report as learning correct answer data in a case where it is determined that the first lesion feature matches the second lesion feature, using the registration means.

According to still another aspect of the invention, there is provided a learning data generation support program that causes a computer to function as: storage means for storing a plurality of pieces of image data and an interpretation report with respect to each of the plurality of pieces of image data; extraction means for analyzing a character string of the interpretation report to extract lesion portion information recorded in the interpretation report and a first lesion feature recorded in the interpretation report; analysis means for performing an image analysis process corresponding to the lesion portion information with respect to the image data corresponding to the interpretation report to acquire a second lesion feature based on a result of the image analysis process; determination means for determining whether the first lesion feature matches the second lesion feature; and registration means for registering the image data corresponding to the interpretation report as learning correct answer data in a case where it is determined that the first lesion feature matches the second lesion feature.

The "lesion portion" represents an organ or a tissue. For example, the organ includes the brain, the lungs, the heart, the liver, the kidneys, or the intestines, and the tissue includes blood vessels, lymph glands, or bones.

The "lesion feature" is a feature that appears on an image, and refers to a feature that appears as the shape of a lesion, the size of a lesion, or light and shade or texture of a lesion. The "determining whether the first lesion feature matches the second lesion feature" means determination of whether the same kind of lesion features match each other. For example, in a case where the "size of a lesion" is used as the first lesion feature, the determination is performed through comparison in a case where the second lesion feature is also the "size of a lesion".

The "first lesion feature" is specified using a term obtained from the interpretation report, and the "second lesion feature" is obtained from a result of the image analysis process and is acquired as data such as numbers or characters output from image processing. In the "determining whether the first lesion feature and the second lesion feature match each other", the lesion features may be represented using terms, numbers, characters, numerical values, or combinations thereof that represent lesions. Here, although they do not completely match each other, terms, numbers, characters, numerical values, or combinations thereof capable of being considered to match each other may be appropriately used. For example, even in a case where a term obtained from an interpretation report is a different term that represents the same meaning, it may be determined that the terms match each other. Further, even in a case where a part of a term is different from an original term, in a case where the terms partially match each other under a certain rule as in an obscure search, for example, it may be determined that the terms match each other. Further, with respect to numerical values, in a case where a difference between the numerical values is within a predetermined range, it may be determined that the numerical values match each other.

In a case where the determination means determines that the first lesion feature does not match the second lesion feature, the analysis means may acquire again the second lesion feature obtained by performing the image analysis process with respect to the image data in a state where a parameter of the image analysis process is adjusted, and then, the determination means may perform the determination again.

The learning data generation support apparatus may further comprise: learning means for executing machine learning using the learning correct answer data.

It is preferable that the lesion feature is a feature of an outward shape of a lesion.

It is preferable that the extraction means analyzes the interpretation report using natural language processing.

It is preferable that the extraction means extracts an organ in which a lesion is present and a range of the organ in which the lesion is present, as the lesion portion information and the analysis means performs an organ recognition process with respect to the image data to recognize an organ, and performs a lesion analysis process with respect to the range of the organ in which the lesion is present to acquire the second lesion feature.

It is preferable that the extraction means extracts a tissue in which a lesion is present and a range of the tissue in which the lesion is present, as the lesion portion information and the analysis means performs a tissue recognition process with respect to the image data to recognize a tissue, and performs a lesion analysis process with respect to the range of the tissue in which the lesion is present to acquire the second lesion feature.

According to the invention, since a character string of an interpretation report is analyzed to extract lesion portion information recorded in the interpretation report and a first lesion feature recorded in the interpretation report, an image analysis process is performed with respect to image data corresponding to the interpretation report to acquire a second lesion feature, and in a case where it is determined that the first lesion feature matches the second lesion feature, the image data is registered as learning correct answer data, it is possible to automatically acquire a large amount of various correct answer data necessary for deep learning.

DETAILED DESCRIPTION

Figure 1:
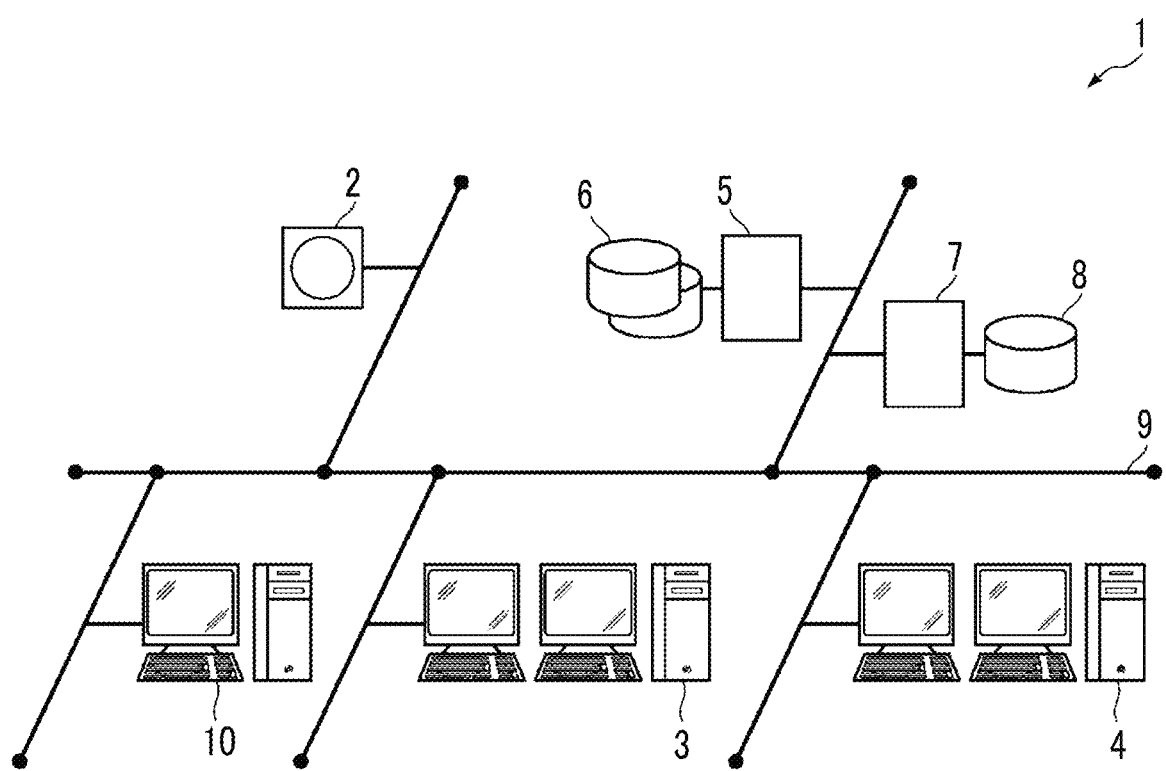
FIG. 1 is a diagram showing a schematic configuration of a medical information system.

FIG. 1 shows a schematic configuration of a medical information system 1 in which a learning data generation support apparatus is introduced, in an embodiment of the invention. As shown in FIG. 1, the medical information system 1 is a system for performing imaging and storage of an inspection target portion of a subject, interpretation of a captured image and creation of an interpretation report from a radiologist in a radiology department, and browsing of the interpretation report and detailed observation of an image that is an interpretation target from a doctor in a diagnosis and treatment department that is a client, on the basis of an inspection order given from the doctor in the diagnosis and treatment department using a known ordering system. The medical information system 1 is configured so that a modality 2, a radiologist workstation 3, a diagnosis and treatment department workstation 4, an image management server 5, an image database 6, an interpretation report server 7, and an interpretation report database 8 are connected to each other in a communicable state through a network 9. In each device, an application program for causing the device to function as a component of the medical information system 1 is installed. Further, the application program may be installed from a recording medium such as a CD-ROM, or may be installed after being downloaded from a storage of a server connected through a network such as the Internet.

The modality 2 includes a device that images an inspection target portion of a subject to generate an inspection image that represents the inspection target portion, and adds accessory information regulated in the DICOM standard to the inspection image for output. As a specific example, a CT apparatus, an MRI apparatus, a positron emission tomography (PET) apparatus, an ultrasonic apparatus, or a CR apparatus that uses a flat panel detector (FPD), or the like may be used.

The radiologist workstation 3 is a computer that is used by a radiologist for interpretation of an image or creation of an interpretation report in a radiology department, and includes a known hardware configuration such as a central processing unit (CPU), a main storage, an auxiliary storage, an input/output interface, a communication interface, an input device, a display device, a data bus, and the like. Further, in the radiologist workstation 3, a known operation system or the like is installed. As the display device, one or plural high definition displays are provided. In the radiologist workstation 3, respective processes such as transmission request of an image with respect to the image management server 5, display of an image received from the image management server 5, automatic detection and highlighting of a lesion likeliness portion in an image, and creation and display of an interpretation report, and the like are performed by executing a software program for the respective processes. Further, the radiologist workstation 3 transmits a generated interpretation report to the interpretation report server 7 through the network 9, and requests registration of the interpretation report into the interpretation report database 8.

The diagnosis and treatment department workstation 4 is a computer that is used by a doctor in a diagnosis and treatment department for detailed observation of an image, browsing of an interpretation report, browsing and input of an electronic medical record, and the like, and includes a known hardware configuration such as a CPU, a main storage, an auxiliary storage, an input/output interface, a communication interface, an input device, a display device, a data bus, and the like. Further, in the diagnosis and treatment department workstation 4, a known operation system or the like is installed. As the display device, one or plural high definition displays are provided. In the diagnosis and treatment department workstation 4, respective processes such as browsing request of an image with respect to the image management server 5, display of an image received from the image management server 5, automatic detection and highlighting of a lesion likeliness portion in an image, browsing request of an interpretation report with respect to the interpretation report server 7, display of an interpretation report received from the interpretation report server 7, and the like are performed by executing a software program for the respective processes. Further, the diagnosis and treatment department workstation 4 transmits a motion picture in endoscopy or the like performed in each diagnosis and treatment department to the image management server 5 through the network 9, and requests registration of the motion picture into the image database 6.

The image management server 5 has a configuration in which a software program that provides a function of a database management system (DBMS) is installed in a general-purpose computer. The image management server 5 is provided with a large capacity storage that configures the image database 6. The storage may be a large capacity hard disk drive connected to the image management server 5 through a data bus, or may be a disk device connected to a network attached storage (NAS) or a storage area network (SAN) connected to the network 9.

In the image database 6, inspection images (image data) obtained by imaging a plurality of patients using the modality 2 and accessory information are registered. The accessory information includes information such as an image identification (ID) for identifying each image, a patient ID for identifying a subject, an inspection ID for identifying inspection, a unique identification (UID) allocated to each inspection image, an inspection date on which an inspection image is generated, an inspection time point, the type of a modality used in inspection for acquiring the inspection image, patient information such as a name, an age, and a gender of a patient, an inspection portion (imaging portion), an imaging condition (the presence or absence of usage of a contrast medium, a radiation dose, or the like), and serial numbers or the like in acquiring a plurality of tomographic images in one inspection.

Further, in a case where a browsing request is received from the radiologist workstation 3 through the network 9, the image management server 5 retrieves an inspection image registered in the above-described image database 6, and transmits the extracted inspection image to the radiologist workstation 3 that is a request source.

The interpretation report server 7 has a configuration in which a software program that provides a function of a database management system (DBMS) is installed in a general-purpose computer. In a case where a registration request of an interpretation report is received from the radiologist workstation 3, the interpretation report server 7 registers the interpretation report into the interpretation report database 8 in accordance with a database format.

In the interpretation report database 8, an interpretation report in which information such as an image ID for identifying an interpretation target image or a representative image, a radiologist ID for identifying an image diagnosis doctor who performs interpretation, a lesion name, lesion position information, a doctor's opinion, and the degree of conviction of the doctor's opinion is recorded is registered. Further, in the interpretation report, a determination result obtained through a biopsy is recorded.

The network 9 is a local area network through which various devices in a hospital are connected to each other. In a case where the radiologist workstation 3 is provided in another hospital or clinic, the network 9 may be configured to connect local area networks in respective hospitals through the Internet or an exclusive line. In any case, it is preferable that the network 9 has a configuration capable of realizing high-speed transmission of an inspection image, such as an optical network or the like.

Figure 2:
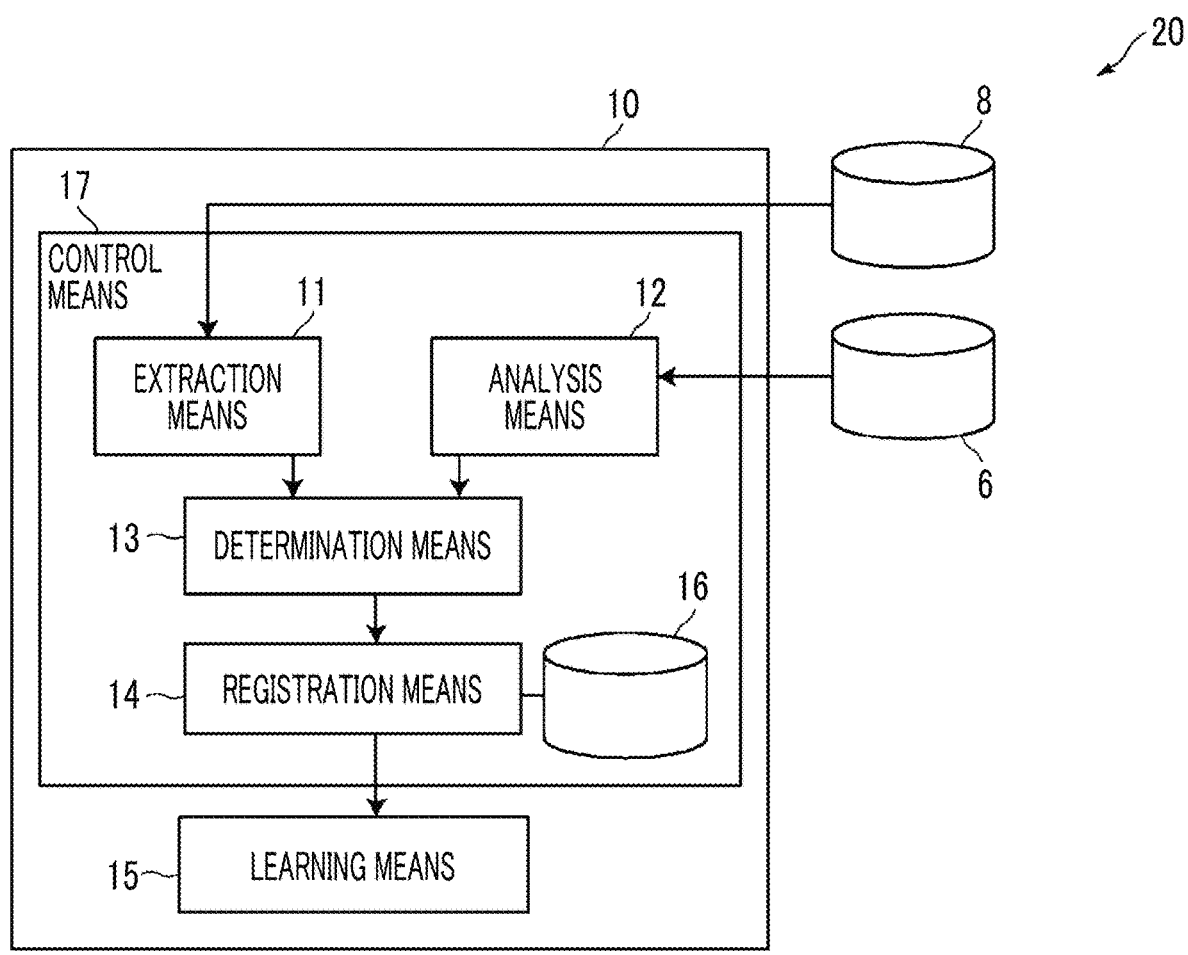
FIG. 2 is a diagram showing a schematic configuration of a learning data generation support apparatus of the invention.
Figure 3:
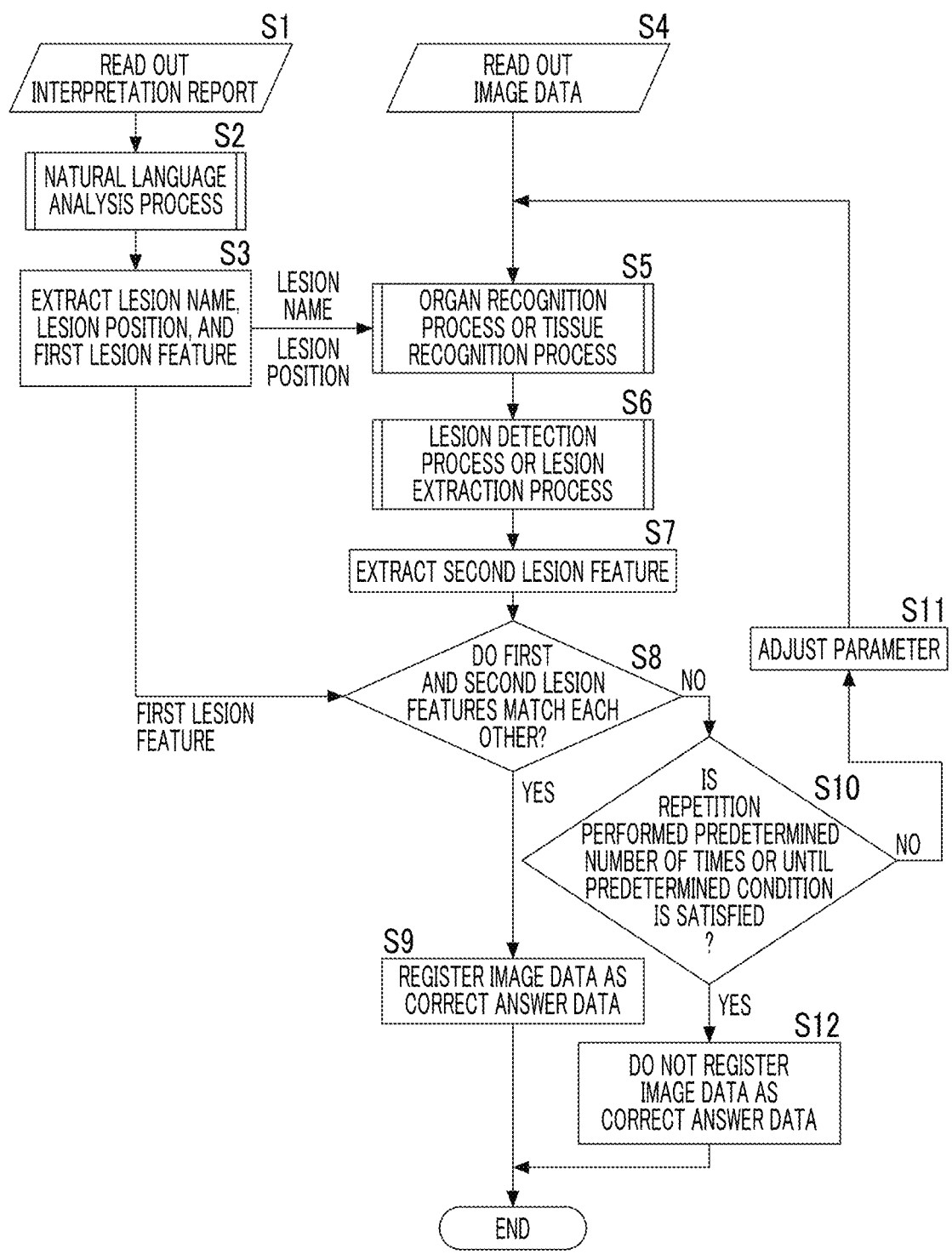
FIG. 3 is a flowchart showing a flow of a process of registering correct answer data.

Next, the learning data generation support apparatus 20 of the invention will be described in detail with reference to FIGS. 1 to 3. FIG. 2 is a functional block diagram of the correct answer data discrimination device 10 that configures the learning data generation support apparatus 20, and FIG. 3 is a flowchart showing a flow of a process of the learning data generation support apparatus 20.

The learning data generation support apparatus 20 of the invention includes the correct answer data discrimination device 10 connected to the network 9, the image database 6, and the interpretation report database 8 (see FIG. 1). The image database 6 and the interpretation report database 8 function as storage means of the invention.

The correct answer data discrimination device 10 is configured of a general-purpose computer, and includes a known hardware configuration such as a CPU, a main storage, an auxiliary storage, an input/output interface, a communication interface, an input device, a display device, a data bus, and the like. In the correct answer data discrimination device 10, a known operation system or the like is installed. Further, the correct answer data discrimination device 10 performs transmission and reception of data with respect to the image database 6 connected to the network 9 and the interpretation report database 8 through a communication interface.

As shown in FIG. 2, the correct answer data discrimination device 10 includes extraction means 11, analysis means 12, determination means 13, registration means 14, a registration unit 16, learning means 15, and control means 17.

The extraction means 11 analyzes a character string of an interpretation report to extract lesion portion information recorded in the interpretation report and a feature of a lesion (a first lesion feature) recorded in the interpretation report. Specifically, the extraction means 11 performs natural language processing, divides a sentence in the interpretation report into words, and analyzes the order of the words, to thereby acquire the lesion portion information. Terms such as a lesion portion name, a lesion name or a lesion feature are registered in advance as necessary, and content written in the report is extracted from a character string that matches the terms.

The lesion portion information includes organ information on an organ in which a lesion is present (or tissue information on a tissue) and position information on the position of a lesion portion indicating a location where a lesion is present on an image space. The organ information (or tissue information) may be information from which an organ (or tissue) can be estimated, such as a name of the organ (or tissue) or a lesion name recorded in an interpretation report. The lesion portion position information includes coordinates of a central position of a lesion portion (for example, barycentric coordinates), the position or a range of a lesion in an organ (or tissue) (for example, a right upper lobe in the case of the lung, a lymph node #13R in the case of the lymph gland), a range of slices in which a lesion portion is present in the case of a three-dimensional image formed by a plurality of tomographic images, or the like. Further, the position information may be information from which the position of a lesion portion can be specified by combination of the above positions or ranges. The position information is not limited thereto, and may be any information from which a position in which a lesion written in an interpretation report is present can be specified.

Further, the lesion feature is a feature that represents a feature of an outward shape of a lesion and appears as a shape of a lesion portion that appears on an image, light and shade of the lesion portion, or a texture of the lesion portion. For example, in the case of a pulmonary nodule, terms that represent tumor features such as a "limbic spine form", or a "marginal branching form", or "marginal alignment" may be used as terms that represent lesion features. Further, in the case of a disease of a lymph node, "swelling" or the like may be used as a term that represents a lesion feature. Further, the lesion feature may include the size of a lesion.

The analysis means 12 performs an image analysis process corresponding to lesion portion information obtained from an interpretation report with respect to image data corresponding to the interpretation report to acquire a second lesion feature on the basis of a result of the image analysis process. For example, in a case where a lesion name and position information are extracted as lesion portion information, first, the analysis means 12 specifies an organ (or tissue) in which a lesion is present from the lesion name, and extracts the organ (or tissue) from the image data using an organ recognition process (or tissue recognition process). Further, the analysis means 12 detects or extracts, using a lesion analysis process for various lesions corresponding to a target organ (or target tissue) from the extracted organ (or tissue), the size of a lesion that is present at a position in an organ (or tissue) corresponding to position information extracted from an interpretation report and a lesion feature (second lesion feature) of the lesion. The organ recognition process (or tissue recognition process) and the lesion analysis process may employ a graph cut. For example, a method disclosed in Japanese Patent No. 4493679 may be used.

The determination means 13 determines whether lesion portion information and a first lesion feature extracted from an interpretation report match lesion portion information and a second lesion feature extracted from image data. Whether or not the lesion features match each other is determined on the basis of whether the first lesion feature obtained from a term that represents a feature of a tumor or a state of an organ (or a state of a tissue) matches a result obtained by the analysis means 12. The term that represents the first lesion feature may be prepared in advance through a medical term dictionary and a plurality of terms that represent the same feature or state may be registered in a dictionary. Then, in a case where a term recorded in the interpretation report represents the same feature or state, the terms may be considered as the same terms, and whether the first lesion feature obtained from the term matches the result (second lesion feature) obtained by the analysis means 12 may be determined. Further, under a certain rule, even in a case where a term does not completely match a term in a dictionary, whether the first lesion feature obtained from the term matches the result obtained by the analysis means 12 may be determined using the most similar term in the dictionary. Further, with respect to the size of a lesion, since there is a case where the size slightly varies according to a measurement position (for example, a position where the diameter of the lesion is measured, or the like) or a measurement method, in a case where an error is within a determined range, it may be determined that the matching is achieved.

Further, with respect to the determination of whether the lesion portion information extracted from the interpretation report matches the lesion portion information obtained by the analysis means 12, in a case where the determination is performed in coordinates in an image space (for example, a centroid of a lesion portion), even though the lesion portion information extracted from the interpretation report does not completely match the lesion portion information obtained by the analysis means 12, the determination means 13 determines that the matching is achieved in a case where an error is within a predetermined range. In addition, in a case where a term that represents a range in an organ such as an area of the liver is determined, the term that represents the range is registered in a dictionary, and then, it is determined whether the range obtained from the term matches the lesion portion information obtained by the analysis means 12. Further, even in a case where terms do not completely match each other, under a certain rule, it may be determined whether the matching is achieved using the most similar term in the dictionary. Further, for example, in a case where a tumor is present in a border between areas in the liver, there is a case where an area written in an interpretation report deviates from an area obtained by the analysis means 12. In this way, in a case where the tumor is present in the border between the areas, even in the case of an adjacent area, it may be determined that the matching is achieved. Further, in a case where there is additional information relating to a position in the interpretation report, the position may be specified using the information.

In a case where the determination means 13 determines that the lesion feature extracted from the interpretation report matches the lesion feature extracted from the image data, the registration means 14 registers image data as learning correct answer data in the registration unit 16. The registration unit 16 is configured of a large-capacity storage device for storing image data. Alternatively, the registration unit 16 may record only IDs of the image data.

The control means 17 controls processing flows of the analysis means 12, the determination means 13, and the registration means 14. In a case where the determination means 13 determines that the first lesion feature and the second lesion feature match each other, the procedure proceeds to the registration means 14, but in a case where the determination means 13 determines that the first lesion feature and the second lesion feature do not match each other, the procedure returns to the analysis means 12 to execute the image analysis process while adjusting a parameter. For example, in a case where there is a difference that is equal to or larger than a predetermined reference value as a result of comparison of the size of a tumor recorded in an interpretation report and the size of a tumor obtained by an image analysis process (for example, in a case where the size of the tumor recorded in the interpretation report is two or more times larger than the size of the tumor obtained by the image analysis process), the image analysis process is executed again after a calculation method of t-link or n-link in a graph cut is adjusted as disclosed in Japanese Patent No. 4493679, for example. A difference in density or light and shade appears in an image due to a difference between imaging conditions or modalities, but it is possible to obtain a correct result by repeatedly performing an image analysis process while adjusting a parameter as described above.

Further, in a case where the first lesion feature and the second lesion feature do not match each other even though the control means 17 adjusts the parameter and repeats the image analysis process a predetermined number of times or until a predetermined condition is satisfied, the procedure is terminated without causing the procedure to proceed to the registration means 14. Alternatively, in a case where the first lesion feature and the second lesion feature do not match each other even though the parameter is adjusted a predetermined number of times until a predetermined condition is satisfied to repeat the image analysis process, the procedure may be terminated without proceeding to the registration means 14. Whether or not the predetermined condition is satisfied may be determined according to whether the adjustment is performed within a range where a parameter value is changeable, or may be determined according to whether the adjustment is performed within a range determined according to a predetermined rule such as a combination of one parameter value and another parameter value. Specifically, in order to adjust a parameter, a parameter value may be repeatedly changed at a predetermined interval to perform an image analysis process.

Hereinafter, a registration method of correct answer data will be described in detail using a flowchart of FIG. 3 with reference to examples of a lung disease and a lymph node disease.

As a first case, an example of a lung disease will be described. First, an interpretation report of a patient A of a lung disease is extracted from an interpretation report database 8 (S1).

Then, natural language processing is executed with respect to the interpretation report by the extraction means 11 (S2), to thereby extract character strings corresponding to "lesion name", "lesion portion position information", "size", and "tumor feature", respectively (S3). In a case where "there is a limbic-spine-form pulmonary nodule of 2.5 cm in a right upper lobe" is recorded in the interpretation report, "pulmonary nodule" is extracted as a character string corresponding to the "lesion name", "right upper lobe" is extracted as a character string corresponding to the "lesion portion position information", "2.5 cm" is extracted as a character string corresponding to the "size", and the "limbic spine form" is extracted as a character string corresponding to the "tumor feature". Further, the "size" and the "tumor feature" are extracted as the first lesion feature.

On the other hand, for example, a CT image is extracted from the image database 6 as image data (S4). Since the lesion name extracted from the interpretation report is "pulmonary nodule", the analysis means 12 performs a lung field recognition process with respect to the CT image (S5). Since the lesion portion position information in the interpretation report indicates "right upper lobe", the analysis means 12 performs a lesion analysis process for a pulmonary nodule in the extracted lung field region (S6). As a result of the lesion analysis process, in a case where an abnormal shadow having a high possibility of a pulmonary nodule is detected, any one of a "limbic spine form", a "marginal branching form", "marginal alignment", and the like is output as a tumor feature of the detected abnormal shadow. Further, the size of the detected abnormal shadow is measured, and then, the size and the tumor feature are extracted as a lesion feature (the second lesion feature) (S7).

Then, the determination means 13 determines whether a pulmonary nodule is detected at a place corresponding to the right upper lobe or in the vicinity thereof by the analysis means 12, whether the size of the detected pulmonary nodule is about 2.5 mm, and whether a tumor feature that appears in a margin of the pulmonary nodule shows a "limbic spine form" (S8). In a case where the size of the pulmonary nodule detected by the analysis means 12 is about 2.5 mm and the tumor feature shows the "limbic spine form", it is determined that the tumor feature matches the tumor feature of the interpretation report (YES in S8). With respect to the size, since there is a case where the size slightly varies according to a measurement position of the diameter, a range of sizes capable of being considered as approximately the same sizes may be used. Further, a CT image for which it is determined that the tumor feature matches the tumor feature of the interpretation report is registered as correct answer data by the registration means 14 (S9).

In addition, in a case where the lesion portion position information written in the interpretation report corresponds to a boundary between the "right upper lobe" or a "right central lobe", for example, it may be determined that the position of the lesion portion detected by the analysis means 12 is the "right central lobe" instead of the "right upper lobe". In this case, the lesion portion position information does not show matching, but in a case where the lesion portion position information corresponds to an adjacent region, the determination may be performed in combination with information relating to a different position recorded in the interpretation report.

On the other hand, even though the pulmonary nodule is detected by the analysis means 12 at the same position as the position extracted from the interpretation report, for example, in a case where the size of the tumor recorded in the interpretation report is two or more times larger than the size of the tumor extracted by the analysis means 12, it cannot be determined that the tumors are the same (NO in S8 and NO in S10), a parameter for an image analysis process, particularly, a parameter relating to a lesion analysis process for various lesions is adjusted (S11), and then, the lesion analysis process that is the image analysis process is performed again (S6). In a case where the sizes are different from each other even though the parameter is adjusted, the parameter is adjusted again. The adjustment of the parameter is performed according to a predetermined rule, and the image analysis process is repeatedly performed while changing the parameter (S5 to S11). In a case where it cannot be determined that the tumors are the same (NO in S8 and YES in S10) even though the image analysis process is repeatedly performed, image data is not registered as correct answer data (S12). The repetition is performed a predetermined number of times. Alternatively, the repetition may be performed until a predetermined condition is satisfied (S10). In this embodiment, the procedure returns to the organ recognition of S5 after the parameter is adjusted, but the procedure may return to the lesion analysis process of S6 according to a condition in which it is determined that the matching is not achieved.

Alternatively, since tumor features are different from each other in a case where margin features are different from each other, image data is not registered as correct answer data. Hereinbefore, a case where the image analysis process is repeatedly performed while changing a parameter with respect to a size has been described, but in a case where margin features do not match each other, similarly, it is preferable that the image analysis process is repeatedly performed while changing a parameter. Further, in a case where a pulmonary nodule is not detected by the analysis means 12, similarly, image data is not registered as correct answer data.

As a second case, an example of a disease of the lymph gland will be described. First, an interpretation report of a patient B of lymphoma is extracted from the interpretation report database 8 (S1).

Figure 4:
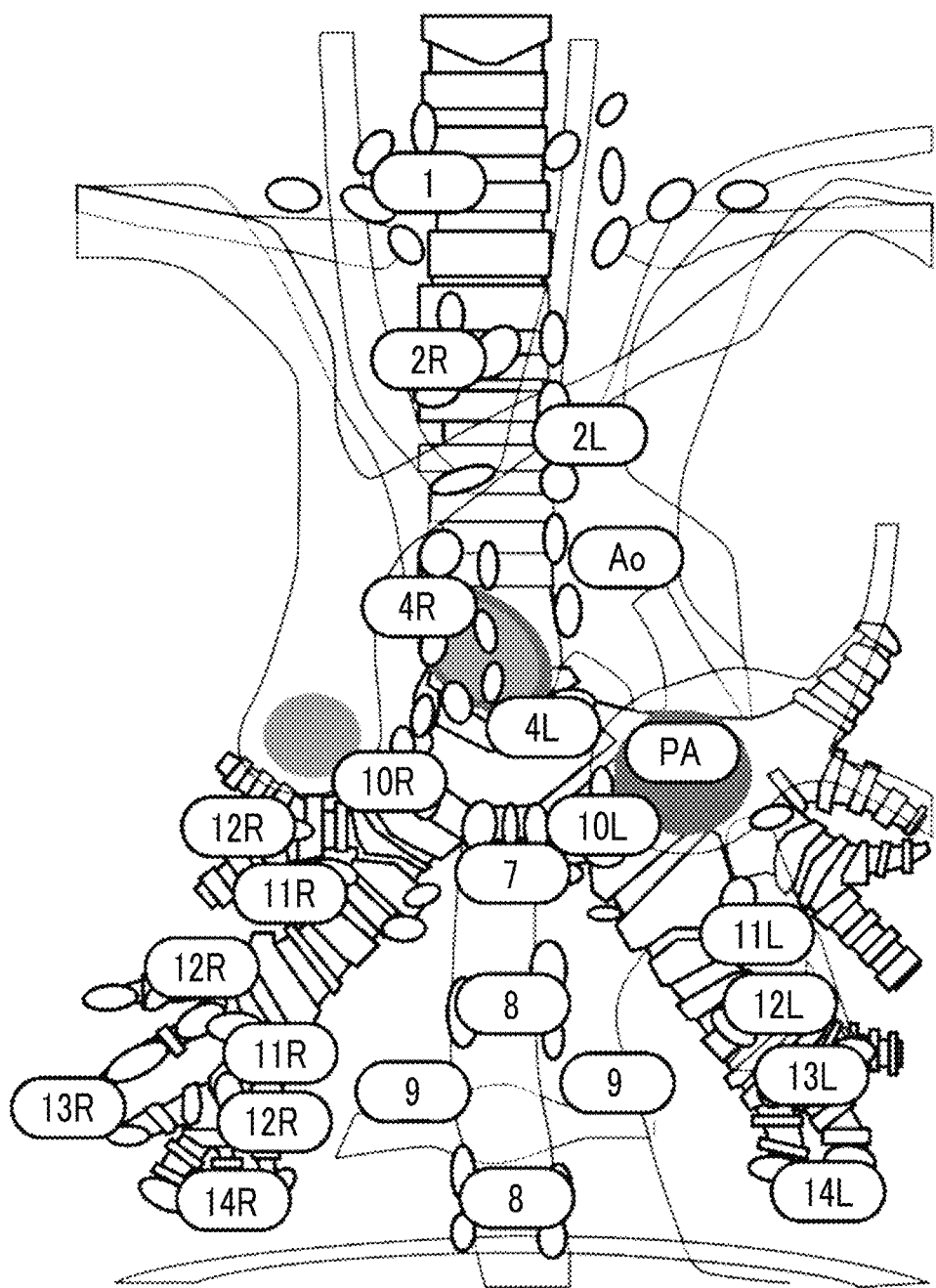
FIG. 4 is a schematic view showing positions of lymph nodes.

Then, natural language processing is executed with respect to the interpretation report using the extraction means 11 (S2), to extract character strings corresponding to "tissue information", "lesion portion position information", "size", and "lesion feature", respectively. In a case where "lymph node #13R is swelling" is recorded in the interpretation report, "lymph" is extracted as a character string corresponding to the "organ information", "lymph node #13R" is extracted as a character string corresponding to the "lesion portion position information", and "swelling" is extracted as a character string corresponding to the "lesion feature (S3). FIG. 4 shows a schematic view showing positions of lymph nodes. "1" in FIG. 4 represents a lymph node on a collarbone, "2" and "4" represent upper juxta-respiratory lymph nodes, "7" represents a tracheal branching lymph node, "8" represents a juxta-esophageal lymph node, "9" represents a pulmonary ligament lymph node", "10" represents a main bronchus surrounding lymph node", "11" represents an inter-leaf bronchus lymph node, "12" represents a leaf bronchus surrounding lymph node, "13" represents an area bronchus surrounding lymph node, "14" represents a sub-region bronchus surrounding lymph node, "Ao" represents the aorta, "PA" represents the pulmonary artery, and "L" and "R" represent left and right. These character strings are recorded in the interpretation report as the lesion portion position information on the lymph nodes.

On the other hand, a CT image is extracted from the image database 6 as image data (S4). Since tissue information extracted from the interpretation report is "lymph", the analysis means 12 performs a lymph gland recognition process with respect to the CT image (S5). Further, in the lymph gland recognition process, as shown in FIG. 4, a function of identifying each lymph node is provided. The position of each lymph node may be specified from correspondence with the position of bronchus. Since the lesion portion position information of the interpretation report corresponds to "lymph node #13R", the analysis means 12 performs a lesion analysis process with respect to the position of the lymph node #13R in the extracted lymph (S6). As a result of the lesion analysis process, a place where the lymph node is more swelling than usual is detected (S7).

Then, in a case where the swelling is detected at the position of the lymph node #13R in the analysis means 12, the determination means 13 determines that the CT image is correct answer data (YES in S8). In a case where the determination means 13 determines that a first lesion feature and a second lesion feature match each other, the registration means 14 registers image data determined as the correct answer data in the registration unit 16 as correct answer data (S9).

On the other hand, in a case where the swelling is not detected at the position of the lymph node #13R in the analysis means 12 (NO in S8 and NO in S10), the image analysis process is repeatedly executed after changing a parameter of the image analysis process (S11). Even though the image analysis process is repeatedly performed until the repetition reaches a predetermined number of times or until a predetermined condition satisfies (YES in S10), in a case where the swelling is not detected at the position of the lymph node #13R, image data is not registered as correct answer data (S12).

The learning means 15 performs machine learning based on a neural network using the image data registered in the registration unit 16 as the correct answer data by the registration means 14. Specifically, for example, by using a convolutional neural network, or the like, an image recognition device may be generated.

As specifically described above, it is possible to a large amount of various correct answer data necessary for machine learning by using image data stored in a medical image management system.

What is claimed is:

1. A learning data generation support apparatus comprising:
storage means, including memory, for storing a plurality of pieces of image data and an interpretation report with respect to each of the plurality of pieces of image data; and
at least one or more processors configured to operate as:
an extraction means for analyzing a character string of the interpretation report to extract lesion portion information recorded in the interpretation report and a first lesion feature recorded in the interpretation report;
an analysis means for performing an image analysis process corresponding to the lesion portion information with respect to the image data corresponding to the interpretation report to acquire a second lesion feature based on a result of the image analysis process;

a determination means for determining whether the first lesion feature matches the second lesion feature; and a registration means for registering the image data corresponding to the interpretation report as learning correct answer data in a case where it is determined that the first lesion feature matches the second lesion feature.

2. The learning data generation support apparatus according to claim 1, wherein in a case where the determination means determines that the first lesion feature does not match the second lesion feature, the analysis means acquires again the second lesion feature obtained by performing the image analysis process with respect to the image data in a state where a parameter of the image analysis process is adjusted, and then, the determination means performs the determination again.

3. The learning data generation support apparatus according to claim 1, wherein the at least one or more processor is further configured to operate as:

learning means for executing machine learning using the learning correct answer data.

4. The learning data generation support apparatus according to claim 1, wherein the lesion feature is a feature of an outward shape of a lesion.

5. The learning data generation support apparatus according to claim 1, wherein the extraction means analyzes the interpretation report using natural language processing.

6. The learning data generation support apparatus according to claim 1, wherein the extraction means extracts an organ in which a lesion is present and a range of the organ in which the lesion is present, as the lesion portion information, and wherein the analysis means performs an organ recognition process with respect to the image data to recognize an organ, and performs a lesion analysis process with respect to the range to acquire the second lesion feature.

7. The learning data generation support apparatus according to claim 1, wherein the extraction means extracts a tissue in which a lesion is present and a range of the tissue in which the lesion is present, as the lesion portion information, and wherein the analysis means performs a tissue recognition process with respect to the image data to recognize a tissue, and performs a lesion analysis process with respect to the range to acquire the second lesion feature.

8. The learning data generation support apparatus according to claim 1, wherein the lesion portion information includes organ information regarding an organ or tissue information regarding a tissue in which a lesion is present and/or position information on the position of a lesion portion indicating a location where the lesion is present on an image; and wherein the image analysis process performs analysis with respect to the organ or the tissue corresponding to the lesion portion information.

9. A learning data generation support method using a learning data generation support apparatus including storage means for storing a plurality of pieces of image data and an interpretation report with respect to each of the plurality of pieces of image data, and at least one or more processors configured to operate as an extraction means, an analysis means, a determination means, and a registration means, the method comprising using the at least one or more processors to perform:

an extraction step of analyzing a character string of the interpretation report to extract lesion portion information recorded in the interpretation report and a first lesion feature recorded in the interpretation report, using the extraction means;

an analysis step of performing an image analysis process corresponding to the lesion portion information with respect to the image data corresponding to the interpretation report to acquire a second lesion feature based on a result of the image analysis process, using the analysis means;

a determination step of determining whether or not the first lesion feature matches the second lesion feature, using the determination means; and a registration step of registering the image data corresponding to the interpretation report as learning correct answer data in a case where it is determined that the first lesion feature matches the second lesion feature, using the registration means.

10. A non-transitory computer-readable storage medium storing therein a learning data generation support program that causes a computer to function as:

storage means for storing a plurality of pieces of image data and an interpretation report with respect to each of the plurality of pieces of image data;

extraction means for analyzing a character string of the interpretation report to extract lesion portion information recorded in the interpretation report and a first lesion feature recorded in the interpretation report;

analysis means for performing an image analysis process corresponding to the lesion portion information with respect to the image data corresponding to the interpretation report to acquire a second lesion feature based on a result of the image analysis process;

determination means for determining whether the first lesion feature matches the second lesion feature; and registration means for registering the image data corresponding to the interpretation report as learning correct answer data in a case where it is determined that the first lesion feature matches the second lesion feature.

* * * * *